US00PP10033P

United States Patent [19]

Greinke

[11] Patent Number: Plant 10,033

[45] Date of Patent: Sep. 16, 1997

[54] DOUBLE IMPATIENS PLANT NAMED 'CHERRY VANILLA'

[75] Inventor: David Greinke, Palmetto, Fla.

[73] Assignee: Ball Horticultural Company, West Chicago, Ill.

[21] Appl. No.: 648,929

[22] Filed: May 16, 1996

[51] Int. Cl.[6] ..... A01H 5/00

[52] U.S. Cl. ..... Plt./87.6

[58] Field of Search ..... Plt./87.6

*Primary Examiner*—James R. Feyrer
*Assistant Examiner*—Kent L. Bell
*Attorney, Agent, or Firm*—C. A. Whealy

[57] ABSTRACT

A distinct cultivar of Double Impatiens plant named Cherry Vanilla, characterized by its large red and white bi-color flowers; consistently double and symmetrical flower form; numerous flowers per plant; long peduncles that hold flowers above the foliage; freely branching plant habit; and mounded and spreading plant form.

2 Drawing Sheets

The present invention relates to a new and distinct cultivar of Double Impatiens plant, botanically known as *Impatiens walleriana,* and hereinafter referred to by the cultivar name Cherry Vanilla.

The new cultivar is a spontaneous mutation of the seed-propagated *Impatiens walleriana* Rosette Mixture. The new cultivar was discovered and selected by the inventor in a controlled environment in Palmetto, Fla., as a single plant among a population of plants of Rosette Mixture. This single plant consistently formed red and white bicolor flowers that were fully double.

Asexual reproduction of the new cultivar by terminal cuttings taken at Palmetto, Fla., has shown that the uniqe features of this new Double Impatiens are stable and reproduced true to type in successive generations.

The following traits have been repeatedly observed and are determined to be the unique characteristics of Cherry Vanilla. These characteristics in combination distinguish the new Double Impatiens as a new and distinct cultivar:

1. Large red and white bi-color flowers.
2. Consistently double and symmetrical flower form.
3. Numerous flowers per plant.
4. Long peduncles that hold flowers above the foliage.
5. Freely branching plant habit.
6. Mounded and spreading plant form.

The new Double Impatiens has not been observed under all possible environmental conditions. The phenotype may vary significantly with variations in environment such as temperature, light level and daylength, without, however, any variance in genotype.

The accompanying colored photographs illustrate the overall appearance and flower color of the new Double Impatiens, showing the colors as true as it is reasonably possible to obtain in colored reproductions of this type.

The first photograph comprises a top perspective view of a typical plant of the new Double Impatiens.

The second photograph comprises a close-up view of the flowers and foliage of the new Double Impatiens.

The following observations, measurements, values, and comparisons describe plants grown in West Chicago, Ill.

In the following description, color references are made to The Royal Horticultural Society Colour Chart except where general terms of ordinary dictionary significance are used.

Botanical classification: *Impatiens walleriana* cultivar Cherry Vanilla.

Parentage: Spontaneous mutation of seed-produced *Impatiens walleriana* Rosette Mixture.

Propagation:

*Type cutting.*—Terminal cuttings.

*Time to initiate roots.*—7 to 10 days at 21C soil temperature.

*Rooting habit.*—Numerous, fibrous, and well-branched

Plant description:

*Form.*—Mounded form, uniform, and spreading.

*Growth habit.*—Moderately vigorous. Freely branching, dense growth. Suitable for 10 to 25-cm containers.

*Foliage description.*—Leaves simple, generally symmetrical, abundant, and flat in aspect. Size, fully matured leaves: Length: About 5.5 cm. Width: About 3.75 cm. Shape: Ovate with acuminate tip. Texture: Smooth. Margin: Crenate. Color: Top side: 147A. Under side: 147B with random red, 183C, spots.

*Stem color.*—Translucent light green, 146A with small red, 183C, spots. Nodal areas reddish, 183C.

Flower description:

*Flower type and habit.*—Large red and white bi-color flowers. Flowers consistently double and symmetrical. Freely and continuously flowering. Flower buds open similar to a rose in fullness. The flowers are borne slightly above the foliage, arising from leaf axils, at least three flowers per peduncle, terminal bud opening first. Numerous flowers per plant.

*Time to flower.*—Flowering generally commences four to six weeks after planting.

*Flowering season.*—Year-round under greenhouse conditions, optimal flowering during spring season in northern hemisphere.

*Flower diameter.*—About 3.5 cm.

*Flower depth (height).*—About 2 cm.

*Flower buds.*—Shape: Ovoid with prominent wing. Color: 144B.

*Petals.*—Quantity: At least 50 per flower. Shape: Round, oblong, or cordate with indentation at tip. Color: Upper side, mature: Iridescent red, 45A, light pink, 55C, and white, 155D. Generally, red at margins and white and/or light pink in center. Actual color patterns vary randomly. Under side, mature: Iridescent coral red, 43B, light pink, 55C, and white, 155D. Generally, coral red at margins and white and/or light pink in center. Actual color patterns vary randomly.

*Sepals.*—Quantity: 2 per flower. Shape: Round with prominent wing. Color: 144B.

*Spur.*—Shape: Narrow and curved. Quantity: One per flower. Length: About 3.5 cm. Color: 144B with red tint.

*Peduncles.*—Length: About 4 cm. Color: 146A.

*Reproductive organs.*—None observed.

Disease resistance: No known Impatiens diseases observed to date on plants grown under commercial greenhouse conditions.

Seed production: Seed production has not been observed.

It is claimed:

1. A new and distinct Double Impatiens plant named Cherry Vanilla, as illustrated and described.

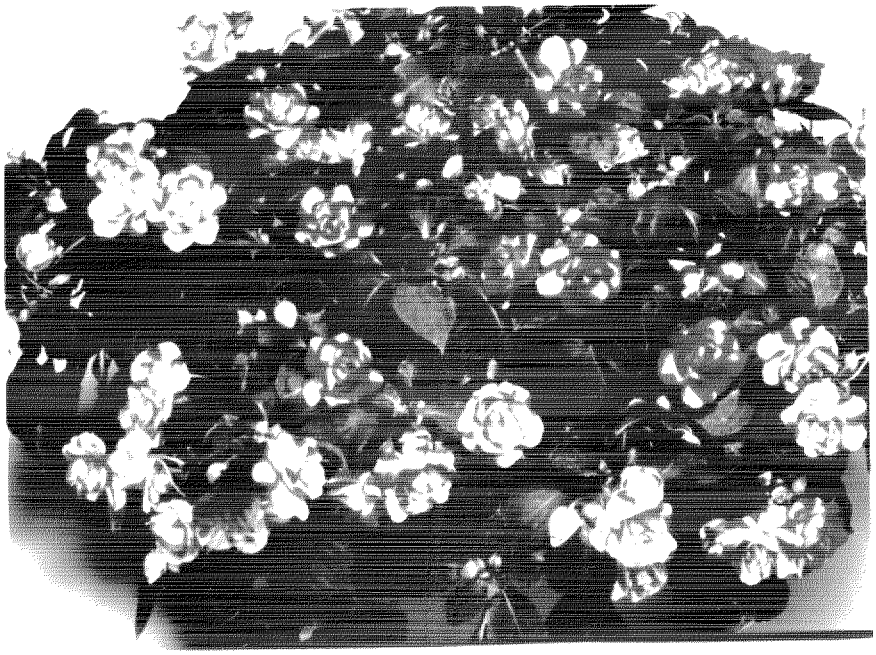

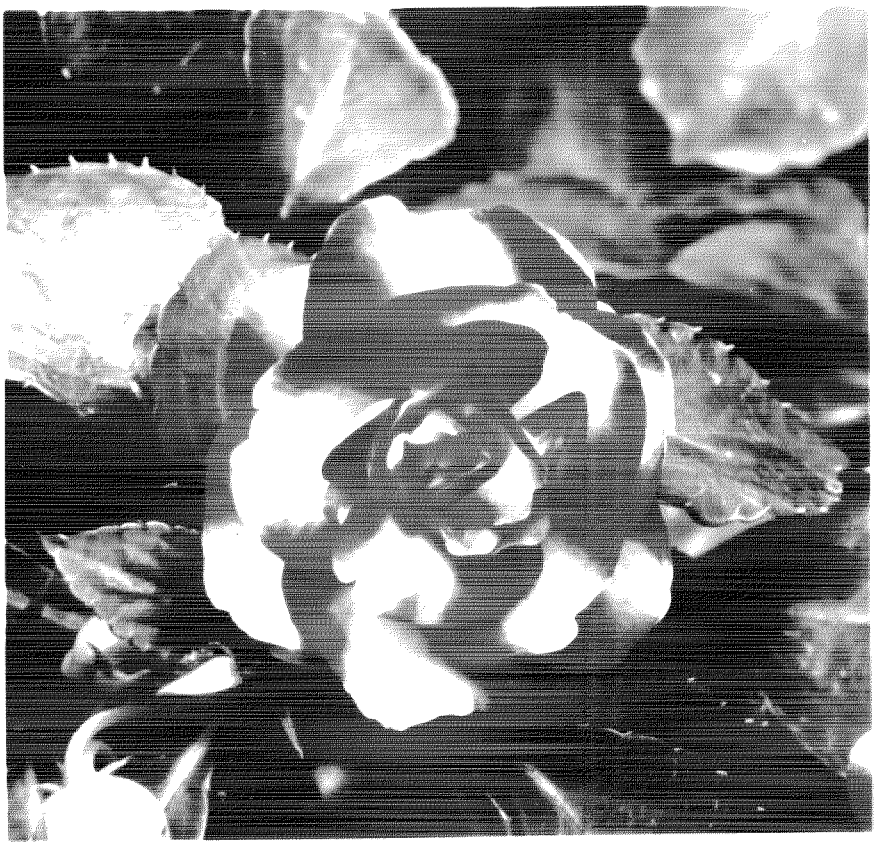

* * * * *